United States Patent [19]

Atkinson et al.

[11] Patent Number: 4,749,699

[45] Date of Patent: Jun. 7, 1988

[54] 5-LIPOXYGENEASE INHIBITORS

[75] Inventors: Joseph G. Atkinson, Montreal; Yvan Guindon, Closse Ile Bizard; Patrice C. Bélanger, Dollard des Ormeaux; Joshua Rokach, Laval, all of Canada

[73] Assignee: Merck Frosst Canada, Inc., Kirkland, Canada

[21] Appl. No.: 887,775

[22] Filed: Jul. 21, 1986

Related U.S. Application Data

[60] Division of Ser. No. 660,595, Oct. 15, 1984, Pat. No. 4,634,766, which is a continuation-in-part of Ser. No. 547,161, Oct. 31, 1983, abandoned.

[51] Int. Cl.$^4$ .............. A61K 31/50; A61K 31/54; A61K 31/495
[52] U.S. Cl. .................. 514/224.5; 514/250; 514/229.8
[58] Field of Search .............. 514/254, 223, 224, 234, 514/250

[56] References Cited

U.S. PATENT DOCUMENTS

| 3,746,707 | 7/1983 | Gulbenk et al. | 544/34 |
| 3,821,213 | 6/1974 | Tong | 544/34 |
| 3,845,044 | 10/1974 | Tong | 544/34 |
| 4,552,874 | 11/1985 | Mardin et al. | 514/222 |

FOREIGN PATENT DOCUMENTS 430462 4/1976 U.S.S.R. .

OTHER PUBLICATIONS

Carter, Chemical Abstracts, vol. 87 (1977) 152146m.
Cheeseman et al, Tetrahedron, vol. 36 (1980), pp. 2681–2683.
Okafor, J., Het. Chem., vol. 18 (1981), pp. 405–407.

Primary Examiner—Stanley J. Friedman
Attorney, Agent, or Firm—Gabriel Lopez; Hesna J. Pfeiffer

[57] ABSTRACT

Compounds of the Formula I:

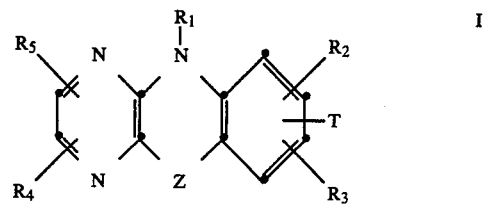

are inhibitors of the mammalian 5-lipoxygenase enzyme system of the arachidonic acid cascade. As such, these compounds are useful therapeutic agents for treating allergic conditions, asthma, cardiovascular disorders and inflammation.

26 Claims, No Drawings

5-LIPOXYGENEASE INHIBITORS

This is a divisional of U.S. Ser. No. 660,595 filed Oct. 15, 1984, now U.S. Pat. No. 4,634,766 which is a C-I-P of U.S. Ser. No. 547,161, filed Oct. 31, 1983, now abandoned.

U.S. Pat. No. 4,634,766 (Atkinson, et al.) is incorporated herein by reference in its entirety.

SUMMARY OF THE INVENTION

The present invention relates to pharmaceutical compositions containing a compound of the Formula I:

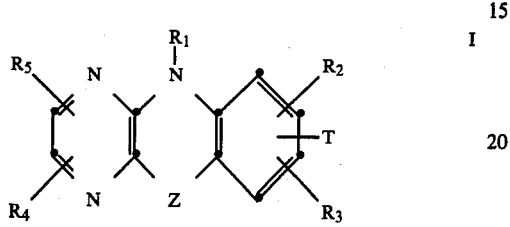

or a phrmaceutically acceptable salt thereof, a method of treatment using said composition and novel compounds encompassed by Formula I.

One embodiment of the present invention is a pharmaceutical composition useful for inhibiting leukotriene biosynthesis or action containing a compound of the Formula I:

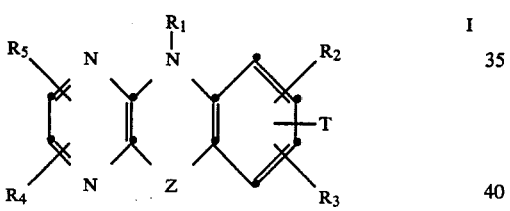

or a pharmaceutically acceptable salt thereof and a pharmaceutically acceptable carrier, wherein:

Z is O, NCN, S, SO or $SO_2$;

$R_1$ is H, $C_1$ to $C_6$ alkyl, benzyl, $C_1$ to $C_6$ acyl, $C_1$ to $C_6$ lower aminoacyl, $C_1$ to $C_6$ alkylacyloxy-$C_1$ to $C_6$ alkyl (for example, $-CH(CH_3)OCOC(CH_3)_3$), $C_1$ to $C_6$ alkoxy-$C_1$ to $C_6$ alkyl (for example, $-CH(CH_3)OC_2H_5$), $-(CH_2)_nCOOR_6$ wherein n is 0 to 4, CN, $C_1$ to $C_6$ alkylacyloxy-$C_1$ to $C_6$ alkoxycarbonyl (e.g. $-COOCH(O_2CCH_3)CH_3$), $-C(R_7)=C(R_7)COOR_6$ or $SO_2R_{10}$;

$R_2$, $R_3$, $R_4$ and $R_5$ are each independently selected from:

(1) hydrogen;
(2) $C_1$ to $C_6$ alkyl;
(3) $C_2$ to $C_6$ alkenyl;
(4) $-(CH_2)_nM$ wherein: n is 0 to 6 and M is
  (a) $OR_{16}$;
  (b) halogen;
  (c) $CF_3$;
  (d) $SR_{16}$;
  (e) phenyl;
  (f) substituted phenyl wherein substituted phenyl is as defined in the definition of $R_{16}$;
  (g) $COOR_6$;
  (h)

(i) tetrazole;
  (j)

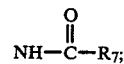

(k) $NR_8R_9$;
  (l) $NHSO_2R_{10}$;
  (m)

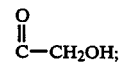

(n) $SOR_{11}$ wherein $R_{11}$ is $C_1$ to $C_6$ alkyl, phenyl, substituted phenyl wherein substituted phenyl is as defined in the definition of $R_{16}$, $(CH_2)_mCOOR_6$ wherein m is 1 to 6, or $CF_3$;
  (o) $CONR_8R_9$;
  (p) $SO_2NR_8R_9$;
  (q) $SO_2R_{13}$ wherein $R_{13}$ is OH, $C_1$ to $C_6$ alkyl, H, phenyl, substituted phenyl wherein substituted phenyl is as defined in the definition of $R_{16}$, $(CH_2)_mCOOR_6$ wherein m is 1 to 6, or $CF_3$;
  (r) $NO_2$;

(s) 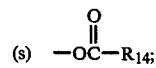

(t) 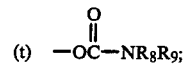

(u) 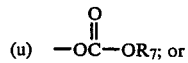

(v) $-CN$;

each $R_{16}$ is independently H; $C_1$ to $C_6$-alkoxy-$C_1$ to $C_6$alkyl; $C_1$ to $C_6$ alkylacyloxy-$C_1$ to $C_6$ alkyl; $C_1$ to $C_6$ alkyl; substituted phenyl wherein the substituents are $C_1$ to $C_3$ alkyl, halogen, CN, $C_1$ to $C_3$ alkoxy, OH, $(CH_2)_nNR_8R_9$ wherein n is 0 to 2, $CF_3$, $COOR_6$, $CH_2COOR_6$; $-(CH_2)_mCOOR_6$ wherein m is 0 to 6; CN; $C_1$ to $C_5$ alkylacyl; $C_1$ to $C_4$ perfluoroalkyl; phenyl; benzyl; or $CH_2$-$R_{12}$ wherein $R_{12}$ is $C_1$ to $C_5$ alkyldimethylamino;

each $R_6$ is independently H, $C_1$ to $C_6$ alkyl, benzyl or phenyl;

each $R_{14}$ is independently H, $C_1$ to $C_6$ alkyl, $C_1$ to $C_6$ alkoxy, $C_1$ to $C_6$ alkylacyloxy-$C_1$ to $C_6$ alkoxy, $(CH_2)_nCOOR_6$ wherein n is 0 to 4, phenyl, substituted phenyl wherein substituted phenyl is as defined in the definition of $R_{16}$, or is such that $R_{14}COOH$ is an essential amino acid;

each $R_8$ and $R_9$ is independently H, phenyl, substituted phenyl wherein substituted phenyl is as defined in the definition of $R_{16}$, or $C_1$ to $C_4$ alkyl, or $R_8$ and $R_9$ may be joined through the N to form a heterocycloalkyl of 5 to 8 ring atoms (for example, pyrrolidino, piperidino); and each $R_7$ is independently H, $C_1$ to $C_6$ alkyl, benzyl, phenyl or $C_1$ to $C_6$ alkylacyloxy-$C_1$ to $C_6$ alkoxy;

each $R_{10}$ is independently OH, $C_1$ to $C_6$ alkyl, $C_1$ to $C_6$ alkoxy, phenyl or p-tolyl;

or any two of $R_1$, $R_2$, $R_3$, $R_4$ or $R_5$ may be joined to form an additional ring of 5 to 7 members, said ring optionally containing a carbonyl group as a substituent, optionally containing a hydroxyl group as a substituent, and optionally having 1 or 2 double bonds, wherein if $R_1$ is a constituent of the ring, one member is nitrogen and the others are carbon and if $R_1$ is not a constituent of the ring, all the members are carbon; and T is hydrogen or $OR_{15}$ wherein $R_{15}$ is hydrogen, $C_1$ to $C_6$ alkyl, $C_1$ to $C_6$ alkylacyl, phenyl-$C_1$ to $C_8$-alkylacyl, $SO_2R_{10}$, arylsulfonyl, —CO-phenyl or substituted phenyl wherein substituted phenyl is as defined in the definition of $R_{16}$.

A preferred embodiment of the Formula I compounds is one wherein Z is O, S, SO or $SO_2$ and wherein n is 0 or 1 in the unit —$(CH_2)_nM$. A more preferred embodiment is wherein Z is O, S, SO or $SO_2$ and wherein n is 0 (zero) in the unit —$(CH_2)_nM$. In both of these embodiments, the remaining substituents are as defined for Formula I.

Another preferred embodiment of the Formula I compounds is one wherein:

Z is O or S;

$R_1$ is H, $C_1$ to $C_6$ alkyl, $C_1$ to $C_6$ acyl, —$(CH_2)_nCOOR_6$ wherein n is 0 to 4, $C_1$ to $C_6$ alkylacyloxy-$C_1$ to $C_6$ alkoxycarbonyl (e.g. —$COOCH(O_2CCH_3)CH_3$), —$C(H)=C(H)COOR_6$, or $SO_2R_{10}$;

$R_2$, $R_3$, $R_4$ and $R_5$ are each independently selected from:
(1) hydrogen;
(2) $C_1$ to $C_6$ alkyl;
(3) —$(CH_2)_nM$ wherein: n is 0 and M is
 (a) $OR_{16}$;
 (b) halogen;
 (c) $CF_3$;
 (d) $NO_2$;

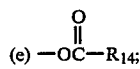

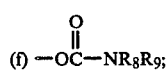

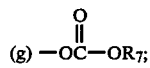

each $R_{16}$ is independently H; $C_1$ to $C_6$-alkoxy-$C_1$ to $C_6$ alkyl; $C_1$ to $C_6$ alkylacyloxy-$C_1$ to $C_6$ alkyl; $C_1$ to $C_6$ alkyl; benzyl; phenyl; substituted phenyl wherein the substituents are $C_1$ to $C_3$ alkyl, halogen, CN, $C_1$ to $C_3$ alkoxy, OH, $(CH_2)_nNR_8R_9$ wherein n is 0 to 2, $CF_3$, $COOR_6$, $CH_2COOR_6$; —$(CH_2)_mCOOR_6$ wherein m is 0 to 6; CN; $C_1$ to $C_5$ alkylacyl; $C_1$ to $C_4$ perfluoroalkyl; or $CH_2$-$R_{12}$ wherein $R_{12}$ is $C_1$ to $C_5$ alkyldimethylamino;

each $R_6$ is independently H, $C_1$ to $C_6$ alkyl, benzyl or phenyl;

each $R_{14}$ is independently H, $C_1$ to $C_6$ alkyl, $C_1$ to $C_6$ alkoxy, $C_1$ to $C_6$ alkylacyloxy-$C_1$ to $C_6$ alkoxy, $(CH_2)_nCOOR_6$ wherein n is 0 to 4, phenyl, substituted phenyl wherein substituted phenyl is as defined in the definition of $R_{16}$, or is such that $R_{14}COOH$ is an essential amino acid;

each $R_8$ and $R_9$ is independently H, phenyl, substituted phenyl wherein substituted phenyl is as defined in the definition of $R_{16}$ or $C_1$ to $C_4$ alkyl, or $R_8$ and $R_9$ may be joined through the N to form a heterocycloalkyl of 5 to 8 ring atoms (for example, pyrrolidino, piperidino); and each $R_7$ is independently H, $C_1$ to $C_6$ alkyl, benzyl, phenyl or $C_1$ to $C_6$ alkylacyloxy-$C_1$ to $C_6$ alkoxy; and each $R_{10}$ is independently OH, $C_1$ to $C_6$ alkyl, $C_1$ to $C_6$ alkoxy, phenyl or p-tolyl;

T is hydrogen or $OR_{15}$ wherein $R_{15}$ is hydrogen, $C_1$ to $C_6$ alkyl, $C_1$ to $C_6$ alkylacyl, phenyl-$C_1$ to $C_8$-alkylacyl, $SO_2$ $R_{10}$, arylsulfonyl, —CO-phenyl or substituted phenyl wherein substituted phenyl is as defined in the definition of $R_{16}$; with the proviso that there is a group $OR_{16}$ located at one of the 6, 7, 8 or 9-positions.

What is claimed is:

1. A method of inhibiting mammalian leukotriene biosynthesis or action which comprises administering to a patient a pharmaceutically effective amount of a composition comprising an effective amount of a compound of Formula I:

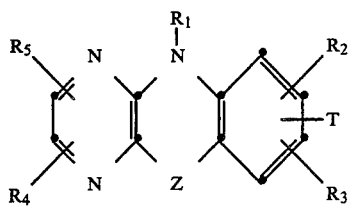

or a pharmaceutically acceptable salt thereof and a pharmaceutically acceptable carrier, wherein:

Z is O, NCN, S, SO or $SO_2$;

$R_1$ is H, $C_1$ to $C_6$ alkyl, benzyl, $C_1$ to $C_6$ acyl, $C_1$ to $C_6$ lower aminoacyl, $C_1$ to $C_6$ alkylacyloxy-$C_1$ to $C_6$ alkyl, $C_1$ to $C_6$ alkoxy-$C_1$ to $C_6$ alkyl, —$(CH_2)_nCOOR_6$ wherein n is 0 to 4, CN, $C_1$ to $C_6$ alkylacyloxy-$C_1$ to $C_6$ alkoxycarbonyl, —$C(R_7)=C(R_7)COOR_6$ or $SO_2R_{10}$;

$R_2$, $R_3$, $R_4$ and $R_5$ are each independently selected from:
(1) hydrogen;
(2) $C_1$ to $C_6$ alkyl;
(3) $C_2$ to $C_6$ alkenyl;
(4) —$CH_2)_nM$ wherein: n is 0 to 6 and M is
 (a) $OR_{16}$;
 (b) halogen;
 (c) $CF_3$;
 (d) $SR_{16}$;
 (e) phenyl;
 (f) substituted phenyl wherein substituted phenyl is as defined in the definition of $R_{16}$;
 (g) $COOR_6$;
 (h)

(i) tetrazole;
 (j)

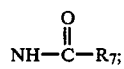

(k) $NR_8R_9$;
 (l) $NHSO_2R_{10}$;

(m)

$$\underset{\text{C}-\text{CH}_2\text{OH};}{\overset{\text{O}}{\|}}$$

(n) $SOR_{11}$ wherein $R_{11}$ is $C_1$ to $C_6$ alkyl, phenyl, substituted phenyl wherein substituted phenyl is as defined in the definition of $R_{16}$, $(CH_2)_mCOOR_6$ wherein m is 1 to 6, or $CF_3$;

(o) $CONR_8R_9$;

(p) $SO_2NR_8R_9$;

(q) $SO_2R_{13}$ wherein $R_{13}$ is OH, $C_1$ to $C_6$ alkyl, H, phenyl, substituted phenyl wherein substituted phenyl is as defined in the definition of $R_{16}$, $(CH_2)_mCOOR_6$ wherein m is 1 to 6, or $CF_3$;

(r) $NO_2$;

$$(s) \quad -\underset{\|}{\overset{\text{O}}{O}}\text{C}-R_{14};$$

$$(t) \quad -\underset{\|}{\overset{\text{O}}{O}}\text{C}-NR_8R_9;$$

$$(u) \quad -\underset{\|}{\overset{\text{O}}{O}}\text{C}-OR_7; \text{ or}$$

(v) —CN;

each $R_{16}$ is independently H; $C_1$ to $C_6$-alkoxy-$C_1$ to $C_6$ alkyl; $C_1$ to $C_6$ alkylacyloxy-$C_1$ to $C_6$ alkyl; $C_1$ to $C_6$ alkyl; substituted phenyl wherein the substituents are $C_1$ to $C_3$ alkyl, halogen, CN, $C_1$ to $C_3$ alkoxy, OH, $(CH_2)_nNR_8R_9$ wherein n is 0 to 2, $CF_3$, $COOR_6$, or $CH_2COOR_6$; $-(CH_2)_mCOOR_6$ wherein m is 0 to 6; CN; $C_1$ to $C_5$ alkylacyl; $C_1$ to $C_4$ perfluoroalkyl; phenyl; benzyl; or $CH_2-R_{12}$ wherein $R_{12}$ is $C_1$ to $C_5$ alkyldimethylamino;

each $R_6$ is independently H, $C_1$ to $C_6$ alkyl, benzyl or phenyl;

each $R_{14}$ is independently H, $C_1$ to $C_6$ alkyl, $C_1$ to $C_6$ alkoxy, $C_1$ to $C_6$ alkylacyloxy-$C_1$ to $C_6$ alkoxy, $(CH_2)_nCOOR_6$ wherein n is 0 to 4, phenyl, substituted phenyl wherein substituted phenyl is as defined in the definition of $R_{16}$, or is such that $R_{14}COOH$ is an essential amino acid;

each $R_8$ and $R_9$ is independently H, phenyl, substituted phenyl wherein substituted phenyl is as defined in the definition of $R_{16}$ or $C_1$ to $C_4$ alkyl, or $R_8$ and $R_9$ may be joined through the N to form a heterocycloalkyl of 5 to 8 ring atoms; and each $R_7$ is independently H, $C_1$ to $C_6$ alkyl, benzyl, phenyl or $C_1$ to $C_6$ alkylacyloxy-$C_1$ to $C_6$ alkoxy;

each $R_{10}$ is independently OH, $C_1$ to $C_6$ alkyl, $C_1$ to $C_6$ alkoxy, phenyl or p-tolyl;

or any two of $R_1$, $R_2$, $R_3$, $R_4$ or $R_5$ may be joined to form an additional ring of 5 to 7 members, said ring optionally containing a carbonyl group as a substituent, optionally containing a hydroxyl group as a substituent, and optionally having 1 or 2 double bonds, wherein if $R_1$ is a constituent of the ring, one member is nitrogen and the others are carbon and if $R_1$ is not a constituent of the ring, all the members are carbon; and T is hydrogen or $OR_{15}$ wherein $R_{15}$ is hydrogen, $C_1$ to $C_6$ alkyl, $C_1$ to $C_6$ alkylacyl, phenyl-$C_1$ to $C_8$-alkylacyl, $SO_2R_{10}$, arylsulfonyl, —CO-phenyl or substituted phenyl wherein substituted phenyl is as defined in the definition of $R_{16}$.

2. A method of claim 1 wherein Z is O.

3. A method of claim 1 wherein Z is S, SO or $SO_2$.

4. A method of claim 1 wherein Z is NCN.

5. A method of claim 1, wherein Z is O, S, SO or $SO_2$ and wherein n is 0 or 1 in the unit $-(CH_2)_nM$.

6. A method of claim 5, wherein n is 0.

7. A method of claim 1, wherein:

Z is O or S;

$R_1$ is H, $C_1$ to $C_6$ alkyl, $C_1$ to $C_6$ acyl, $-(CH_2)_nCOOR_6$ wherein n is 0 to 4, $C_1$ to $C_6$ alkylacyloxy-$C_1$ to $C_6$ alkoxycarbonyl, $-C(H)=C(H)COOR_6$, or $SO_2R_{10}$;

$R_2$, $R_3$, $R_4$ and $R_5$ are each independently selected from:

(1) hydrogen;

(2) $C_1$ to $C_6$ alkyl;

(3) $-(CH_2)_nM$ wherein: n is 0 and M is (a) $OR_{16}$;

(b) halogen;

(c) $CF_3$;

(d) $NO_2$;

$$(e) \quad -\underset{\|}{\overset{\text{O}}{O}}\text{C}-R_{14};$$

$$(f) \quad -\underset{\|}{\overset{\text{O}}{O}}\text{C}-NR_8R_9;$$

$$(g) \quad -\underset{\|}{\overset{\text{O}}{O}}\text{C}-OR_7;$$

each $R_{16}$ is independently H; $C_1$ to $C_6$-alkoxy-$C_1$ to $C_6$ alkyl; $C_1$ to $C_6$ alkylacyloxy-$C_1$ to $C_6$ alkyl; $C_1$ to $C_6$ alkyl; benzyl; phenyl; substituted phenyl wherein the substituents are $C_1$ to $C_3$ alkyl, halogen, CN, $C_1$ to $C_3$ alkoxy, OH, $(CH_2)_nNR_8R_9$ wherein n is 0 to 2, $CF_3$, $COOR_6$, or $CH_2COOR_6$; $-(CH_2)_mCOOR_6$ wherein m is 0 to 6; CN; $C_1$ to $C_5$ alkylacyl; $C_1$ to $C_4$ perfluoroalkyl; or $CH_2-R_{12}$ wherein $R_{12}$ is $C_1$ to $C_5$ alkyldimethylamino;

each $R_6$ is independently H, $C_1$ to $C_6$ alkyl, benzyl or phenyl;

each $R_{14}$ is independently H, $C_1$ to $C_6$ alkyl, $C_1$ to $C_6$ alkoxy, $C_1$ to $C_6$ alkylacyloxy-$C_1$ to $C_6$ alkoxy, $(CH_2)_nCOOR_6$ wherein n is 0 to 4, phenyl, substituted phenyl wherein substituted phenyl is as defined in the definition of $R_{16}$, or is such that $R_{14}COOH$ is an essential amino acid;

each $R_8$ and $R_9$ is independently H, phenyl, substituted phenyl wherein substituted phenyl is as defined in the definition of $R_{16}$ or $C_1$ to $C_4$ alkyl, or $R_8$ and $R_9$ may be joined through the N to form a heterocycloalkyl of 5 to 8 ring atoms; and each $R_7$ is independently H, $C_1$ to $C_6$ alkyl, benzyl, phenyl or $C_1$ to $C_6$ alkylacyloxy-$C_1$ to $C_6$ alkoxy; and each $R_{10}$ is independently OH, $C_1$ to $C_6$ alkyl, $C_1$ to $C_6$ alkoxy, phenyl or p-tolyl;

T is hydrogen or $OR_{15}$ wherein $R_{15}$ is hydrogen, $C_1$ to $C_6$ alkyl, $C_1$ to $C_6$ alkylacyl, phenyl-$C_1$ to $C_8$-alkylacyl, $SO_2R_{10}$, arylsulfonyl, —CO-phenyl or substituted phenyl wherein substituted phenyl is as defined in the definition of $R_{16}$;

with the proviso that there is a group $OR_{16}$ located at one of the 6, 7, 8 or 9-positions.

8. A method of claim 1 wherein the Formula I substituents are selected from:

| Z | $R_1$ | $R_2$ | $R_3$ | $R_4$ | $R_5$ | T |
|---|---|---|---|---|---|---|
| S | H | H | H | H | H | H |
| S | $CH_3$ | H | H | H | H | H |
| S | $CH_2Ph$ | H | H | H | H | H |
| S | H | 3-$NO_2$ | H | H | H | H |
| S | H | 2-Cl | 3-Cl | H | H | H |
| S | H | 3-$NO_2$ | 7-$NO_2$ | H | H | H |
| S | $CH_3$ | 2-$NO_2$ | H | H | H | H |
| S | $CH_3$ | 3-$NO_2$ | H | H | H | H |
| S | n-$C_3H_7$ | 2-Cl | 3-Cl | H | H | H |
| S | n-$C_6H_{13}$ | 2-Cl | 3-Cl | H | H | H |
| S | $CH_2Ph$ | 2-Cl | 3-Cl | H | H | H |
| SO | H | H | H | H | H | H |
| SO | $CH_3$ | H | H | H | H | H |
| SO | H | 2-Cl | 3-Cl | H | H | H |
| SO | H | 3-$NO_2$ | 7-$NO_2$ | H | H | H |
| $SO_2$ | $CH_3$ | H | H | H | H | H |
| $SO_2$ | $CH_2Ph$ | H | H | H | H | H |
| $SO_2$ | $CH_2Ph$ | 2-Cl | 3-Cl | H | H | H |
| O | H | H | H | H | H | H |
| O | H | 2-F | 3-F | H | H | H |
| O | H | 2-Cl | 3-Cl | H | H | H |
| O | H | 2-Br | 3-Br | H | H | H |
| O | H | 2-Cl | 3-Cl | 8-$CH_3$ | H | H |
| N—CN | H | H | H | H | H | H |
| N—CN | $CH_3$ | 2-$CH_3$ | 3-$CH_3$ | H | H | H |
| N—CN | $CH_3$ | H | H | H | H | 7-$OCH_3$ |
| S | H | H | H | H | H | 7-$OCH_3$ |
| S | H | H | H | H | 8-Cl | 7-$OCH_3$ |
| S | $CH_3$ | H | H | H | 8-Cl | 7-$OCH_3$ |
| S | $CH_3$ | H | H | H | 8-Cl | 7-OH |
| S | $CH_3$ | H | H | H | H | 7-$OCH_3$ |
| S | H | H | H | H | H | 7-OH |
| S | $CH_3$ | H | H | H | H | 7-OH |
| SO | H | H | H | H | H | 7-$OCH_3$ |
| SO | $CH_3$ | H | H | H | H | 7-$OCH_3$ |
| S | $SO_2Ph$—p-Me | H | H | H | H | 7-$OCH_3$ |
| $SO_2$ | H | H | H | H | H | 7-$OCH_3$ |
| S | $COCH_3$ | H | H | H | H | 7-$OCH_3$ |
| S | $COCH_3$ | H | H | H | H | H |
| $SO_2$ | H | H | H | H | H | H |
| S | $CH_2CO_2C_2H_5$ | H | H | H | H | H |
| S | $CH_2CO_2H$ | H | H | H | H | H |
| S | $CO_2CH_3$ | H | H | H | H | H |
| S | $CH=CHCO_2CH_3$ | H | H | H | H | H |
| S | H | 2-Cl | H | H | H | H |
| S | H | 3-Cl | H | H | H | H |
| S | H | 8-Cl | H | H | H | H |
| S | H | 2-Me | H | H | H | H |
| S | H | H | H | H | H | 7-$OCH_3$ |
| S | H | H | H | H | 8-Cl | 7-$OCH_3$ |

9. A method of claim 1 wherein the Formula I substituents are selected from:

| Z | $R_1$ | $R_2$ | $R_3$ | $R_4$ | $R_5$ | T |
|---|---|---|---|---|---|---|
| S | $CH_3$ | H | H | H | 8-Cl | 7-$OCH_3$ |
| S | $CH_3$ | H | H | H | 8-Cl | 7-OH |
| S | $CH_3$ | H | H | H | H | 7-$OCH_3$ |
| S | H | H | H | H | H | 7-OH |
| S | $CH_3$ | H | H | H | H | 7-OH |
| SO | H | H | H | H | H | 7-$OCH_3$ |
| SO | $CH_3$ | H | H | H | H | 7-$OCH_3$ |
| S | $SO_2Ph$—p-Me | H | H | H | H | 7-$OCH_3$ |
| $SO_2$ | H | H | H | H | H | 7-$OCH_3$ |
| S | $COCH_3$ | H | H | H | H | 7-$OCH_3$ |
| S | $COCH_3$ | H | H | H | H | H |
| $SO_2$ | H | H | H | H | H | H |
| S | $CH_2CO_2C_2H_5$ | H | H | H | H | H |
| S | $CH_2CO_2H$ | H | H | H | H | H |
| S | $CO_2CH_3$ | H | H | H | H | H |
| S | $CH=CHCO_2CH_3$ | H | H | H | H | H |

10. A method of claim 9 wherein the compound is 7-methoxy-1,4-diaza-10-methylphenothiazine.

11. A method of claim 9 wherein the compound is 7-hydroxy-1,4-diaza-10H-phenothiazine.

12. A method of claim 9 wherein the compound is 7-hydroxy-1,4-diaza-10-methylphenothiazine.

13. A method of claim 9 wherein the compound is 8-chloro-1,4-diaza-7-methoxyphenothiazine.

14. A method of claim 9 wherein the compound is 8-chloro-7-methoxy-1,4-diaza-10-methylphenothiazine.

15. A method of claim 9 wherein the compound is 8-chloro-7-hydroxy-1,4-diaza-10-methylphenothiazine.

16. A method of claim 1 wherein pulmonary conditions are treated or ameliorated.

17. A method of claim 1 wherein inflammation is treated.

18. A method of claim 1 wherein allergies are treated.

19. A method of claim 1 wherein skin conditions are treated.

20. A pharmaceutical composition for inhibiting leukotriene biosynthesis or action comprising an effective amount of a compound of the Formula I':

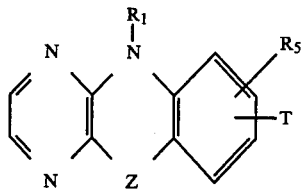

or a pharmaceutically acceptable salt thereof and a pharmaceutically acceptable carrier, wherein the Formula I' substituents are selected from:

| Z   | $R_1$ | $R_5$ | T       |
|-----|-------|-------|---------|
| S   | H     | H     | 7-OCH$_3$ |
| S   | H     | 8-Cl  | 7-OCH$_3$ |
| S   | CH$_3$ | 8-Cl  | 7-OCH$_3$ |
| S   | CH$_3$ | 8-Cl  | 7-OH    |
| S   | CH$_3$ | H     | 7-OCH$_3$ |
| S   | H     | H     | 7-OH    |
| S   | CH$_3$ | H     | 7-OH    |
| SO  | H     | H     | 7-OCH$_3$ |
| SO  | CH$_3$ | H     | 7-OCH$_3$ |

-continued

| Z   | $R_1$ | $R_5$ | T       |
|-----|-------|-------|---------|
| S   | SO$_2$Ph—p-Me | H | 7-OCH$_3$ |
| SO$_2$ | H   | H     | 7-OCH$_3$ |
| S   | COCH$_3$ | H | 7-OCH$_3$ |
| S   | COCH$_3$ | H | H |
| S   | CH$_2$CO$_2$C$_2$H$_5$ | H | H |
| S   | CH$_2$CO$_2$H | H | H |
| S   | CO$_2$CH$_3$ | H | H |
| S   | CH=CHCO$_2$CH$_3$ | H | H |

21. A composition of claim 20 wherein the compound is 7-methoxy-1,4-diaza-10-methylphenothiazine.

22. A composition of claim 20 wherein the compound is 7-hydroxy-1,4-diaza-10H-phenothiazine.

23. A composition of claim 20 wherein the compound is 7-hydroxy-1,4-diaza-10-methylphenothiazine.

24. A composition of claim 20 wherein the compound is 8-chloro-1,4-diaza-7-methoxyphenothiazine.

25. A composition of claim 20 wherein the compound is 8-chloro-7-methoxy-1,4-diaza-10-methylphenothiazine.

26. A composition of claim 20 wherein the compound is 8-chloro-7-hydroxy-1,4-diaza-10-methylphenothiazine.

* * * * *